United States Patent
Manikandan et al.

(10) Patent No.: US 8,614,258 B2
(45) Date of Patent: Dec. 24, 2013

(54) KEGGIN-TYPE STRUCTURE HETEROPOLY COMPOUND-BASED CATALYST COMPOSITIONS AND THEIR USE IN CONVERSION OF SYNTHESIS GAS TO OXYGENATES

(75) Inventors: Palanichamy Manikandan, Pune (IN); Sreenivasa Rao, Pune (IN); David G. Barton, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 13/825,608

(22) PCT Filed: Sep. 26, 2011

(86) PCT No.: PCT/US2011/053202
§ 371 (c)(1),
(2), (4) Date: Mar. 22, 2013

(87) PCT Pub. No.: WO2012/050806
PCT Pub. Date: Apr. 19, 2012

(65) Prior Publication Data
US 2013/0310470 A1    Nov. 21, 2013

Related U.S. Application Data

(60) Provisional application No. 61/391,739, filed on Oct. 11, 2010.

(51) Int. Cl.
C07C 27/00 (2006.01)

(52) U.S. Cl.
USPC ........... 518/714; 518/713; 518/715; 518/716; 518/717; 518/719

(58) Field of Classification Search
USPC ................. 518/513, 514, 515, 516, 517, 519
See application file for complete search history.

(56) References Cited

U.S. PATENT DOCUMENTS

| 4,210,597 A | 7/1980 | Huang |
| 4,607,055 A | 8/1986 | Grazioso et al. |
| 4,607,056 A | 8/1986 | Grazioso et al. |
| 4,616,040 A | 10/1986 | Grazioso et al. |
| 4,749,724 A | 6/1988 | Quarderer et al. |
| 4,825,013 A | 4/1989 | Quarderer et al. |
| 6,127,432 A | 10/2000 | Wegman et al. |
| 6,278,030 B1 | 8/2001 | Vargas et al. |
| 7,923,405 B2 * | 4/2011 | Kharas et al. ............... 502/216 |

FOREIGN PATENT DOCUMENTS

GB    2151616 A    7/1985

OTHER PUBLICATIONS

T. Nakato, et al., Changes of Surface Properties and Water-Tolerant Catalytic Activity of Solid Acid Cs2.5H0.5PW12O40 in Water, Langmuir, 1998, pp. 319-325, vol. 14.
P. Villabrille, et al., Synthesis and characterization of Fe- and Cu-doped molybdovanadophosphoric acids and their application in catalytic oxidation, Applied Catalysis A: General, 2007, pp. 69-76, vol. 324.
C. Rocchiccioli-Deltcheff, et al., Journal of Molecular Catalysis A: Chemical, 1996, pp. 331-342, vol. 114.
O. A. Kholdeeva, et al., Journal of Molecular Catalysis A: Chemical, 1996, pp. 123-130, vol. 114.
K. Eguchi, et al., Journal of Catalysis, 1988, pp. 336-344, vol. 111.
K. Song and M.A. Barteau, Journal of Molecular Catalysis A: Chemical, 2004, pp. 229-236, vol. 212.
N. Dimitratos, et al., Catalysis Today, 2007, pp. 307-316, vol. 122.
PCT/US2011/053202, International Search Report, 2013.
PCT/US2011/053202, International Preliminary Report on Patentability, 2013.
PCT/US2011/053202, Written Opinion of the International Searching Authority, 2013.

* cited by examiner

Primary Examiner — Jafar Parsa

(57) ABSTRACT

Use a transition metal-containing, Keggin-type heteropoly compound as a catalyst to convert synthesis gas to an alcohol, especially a $C_1$-$C_6$ alcohol.

9 Claims, No Drawings

KEGGIN-TYPE STRUCTURE HETEROPOLY COMPOUND-BASED CATALYST COMPOSITIONS AND THEIR USE IN CONVERSION OF SYNTHESIS GAS TO OXYGENATES

This application is a non-provisional application claiming priority from the U.S. Provisional Patent Application No. 61/391,739, filed on Oct. 11, 2010, entitled "KEGGIN-TYPE STRUCTURE HETEROPOLY COMPOUND-BASED CATALYST COMPOSITIONS AND THEIR USE IN CONVERSION OF SYNTHESIS GAS TO OXYGENATES" the teachings of which are incorporated by reference herein, as if reproduced in full hereinbelow.

This invention relates generally to catalyst compositions based upon a Keggin-type structure heteropoly compound and their use in converting synthesis gas (syngas, a mixture of carbon monoxide (CO) and hydrogen ($H_2$)) to oxygenates, especially alcohols that contain from two to six carbon atoms ($C_2$ to $C_6$).

Syngas conversion processes employ a variety of catalysts that, in turn, tend to yield a mixture of products (e.g. hydrocarbons such as ethane and propane and oxygenated hydrocarbons such as methanol, ethanol, propanol and butanol). Those who practice such processes continue to seek improved processes and catalysts which provide a product mixture that favors selectivity to oxygenates over hydrocarbons, with at least some practioners preferring certain oxygenates, such as propanol, over other oxygenates, such as methanol. Such a preference stems, at least in part, from ease of converting $C_2$ to $C_6$ oxygenates to corresponding olefins or, via hydroformylation, to higher oxygenates, relative to challenges in converting methanol to an olefin.

Claude Rocchioccioli-Deltcheff et al., in "Silica-supported 12-molybdophosphoric acid catalysts: Influence of the thermal treatments and of the Mo contents on their behavior, from IR, Raman, X-ray diffraction studies, and catalytic reactivity in the methanol oxidation", *Journal of Molecular Catalysis A: Chemical* 114 (1996), pages 331-342, note that the acidic and oxidizing properties of 12-molybdophosphoric acid ($H_3PMo_{12}O_{40}$) (also known as a "heteropolyacid") are widely used in catalysis and that in many catalytic applications, the active species is deposited on a support such as silica. They teach that the anion $PMo_{12}O_{40}{}^{3-}$ belongs to the well-known Keggin structure.

O. A. Kholdeeva et al., in "Polyfunctional action of transition metal substituted heteropolytungstates in alkene epoxidation by molecular oxygen in the presence of aldehyde". *Journal of Molecular Catalysis A: Chemical* 114 (1996), pages 123-130, study tetrabutylammonium (TBA) salts of substituted heteropolytungstates using transition metal substituents including cobalt (II), iron (III), palladium (II), nickel (II), copper (II), manganese (II), vanadium (V), ruthenium (IV), titanium (IV), cerium (IV) and zirconium (IV).

U.S. Pat. No. 4,210,597 (Huang) teaches preparation of oxygenated compounds by contacting syngas with a solid catalyst that contains rhodium (Rh), tungsten (W) and an alkali metal (e.g. sodium (Na)).

Group VIII metals include iron (Fe), cobalt (Co), nickel (Ni), ruthenium (Ru), rhodium (Rh), palladium (Pd), osmium (Os), iridium (Ir), and platinum (Pt).

U.S. Pat. No. 4,749,724 (Quarderer et al.) discloses a Fischer-Tropsch reaction to form alcohols from syngas using a catalyst containing at least one element selected from Mo, W and Re in free or combined form, an alkali metal or alkaline earth metal promoter, and, optionally, a support. The catalyst may contain limited quantities of carbon oxide hydrogenating components such as zinc (Zn), copper (Cu) and cobalt (Co).

U.S. Pat. No. 4,825,013 (Quarderer et al.) relates to a process for forming an alcohol fraction boiling in the range of motor gasoline that is enriched in higher alcohols. The process includes use of a catalyst comprising a first component comprising Mo, W or a mixture thereof in free or combined form, an alkali or alkaline earth metal element or a mixture thereof in free or combined form, an optional third component comprising Co, Ni or Fe or a mixture thereof in free or combined form, and an optional fourth component comprising a support.

U.S. Pat. No. 4,607,055 (Grazioso et al.) teaches a method for preparing a mixture of lower aliphatic alcohols by reacting syngas with a catalyst comprising Mo, a metal selected from Co, Fe, Ni and silver (Ag), and a promoter selected from potassium (K), cesium (Cs) and rubidium (Rb).

U.S. Pat. No. 4,616,040 (Grazioso et al.) presents teachings related to those of U.S. Pat. No. 4,607,056 by providing for use of copper (Cu) rather than Re.

In some aspects, this invention is a process for converting synthesis gas to an oxygenate, which process comprises contacting a mixture of hydrogen and carbon monoxide with a catalyst based on a transition metal-containing, Keggin-type heteropoly compound under conditions of temperature, pressure and gas hourly space velocity sufficient to convert said mixture to at least one alcohol wherein the alcohol is a one carbon to six carbon alcohol, the catalyst having a structure represented by general formula $M_1[HPA]M_2M_3$ where $M_1$ is at least one metal selected from a group consisting of alkali metals, alkaline earth metals, zinc (Zn), cobalt (Co), iron (Fe), manganese (Mn), nickel (Ni) and copper (Cu); [HPA] is an anion that has a net negative charge and is represented by general formula $[XMo_{12-(x+y)}W_xT_yO_{40}]$ wherein Mo is molybdenum, W is tungsten, T is at least one transition metal selected from vanadium, copper, cobalt, iron, titanium, palladium, ruthenium, and manganese, x=0-12, y=0-3 provided that x+y=0-12 and X is at least one of phosphorous (P), silicon (Si), germanium (Ge), and Co; $M_1$ has a sum net charge equal to net negative charge of HPA; $M_2$ is at least one of rhodium (Rh), palladium (Pd), iridium (Ir), rhenium (Re), ruthenium (Ru), platinum (Pt) and gold (Au); and $M_3$ is at least one alkali or alkaline earth metal, provided that when $M_1$ is an optional material that is an alkali metal or an alkaline earth metal, it is a different alkali metal or alkaline earth metal than $M_3$ and when $M_1$ is cobalt, X is at least one of phosphorous, silicon and germanium. The catalyst preferably includes a support selected from silicas, aluminas, magnesias, zirconias, titanias, or a mixture of two or more of such supports as well as modified supports like zirconia-modified silica ($ZrO_2$—$SiO_2$). See *Journal of Catalysis* Vol 111 (1988), page 336, and Journal of Molecular Catalysis A. vol. 212 (2004), page 229 for teachings that P, Si, Ge and/or Co perform in a similar manner for X.

Particularly preferred catalysts represented by the above general formula include those with any of a) a combination of Cs and Co as $M_1$; b) Li or K as $M_3$; c) $[PMo_{12}O_{40}]$ as HPA (X=P and x=0); and d) Rh as $M_2$.

Preparation of oxygenates from syngas occurs under a combination of conditions. The conditions include a temperature within a range of from 200° C. to 450° C.; a pressure within a range of from 200 psig (1.38 MPa) to 5,000 psig (34.47 MPa), preferably from 200 psig (1.38 MPa) to 3000 psig (20.68 MPa) and more preferably from 300 psig (2.07 MPa) to 1500 psig (10.34 MPa); a gas hourly space velocity (GHSV) of from 300 reciprocal hours ($hr^{-1}$) to 25,000 $hr^{-1}$, preferably from 300 $hr^{-1}$ to 20,000 $hr^{-1}$ and more preferably from 6000 $hr^{-1}$ to 7000 $hr^{-1}$; and a gaseous hydrogen ($H_2$) to carbon monoxide (CO) ratio within a range of from 10:1 to 1:10, preferably from 5:1 to 1:5 with very satisfactory results at a ratio of 1:1.

If desired, syngas may be admixed with an amount of an olefin such as ethylene or propylene prior to contact with the catalyst. When such an olefin contacts the catalyst, at least a portion of the olefin converts to an alcohol or an aldehyde or a mixture of an alcohol and an aldehyde. The amount is preferably within a range of from 1 percent by volume (vol %) to 50 vol %, based upon total volume of syngas plus olefin.

Unsupported Keggin-type heteropoly compounds comprise, consist essentially of, or consist of, $M_1$ in an amount within a range of from 2 wt % to 35 wt %. [HPA] in an amount within a range of from 65 wt % to 98 wt %. $M_2$ in an amount within a range of from 0.01 wt % to 10 wt %, and $M_3$ within a range of from 0 wt % to 10 wt %, each wt % being based upon combined weight of Mo or W, transition metal and alkaline earth metal or alkali metal. Within [HPA], X is present in an amount within a range of from 1 wt % to 4 wt %, W in an amount within a range of from 62 weight percent (wt %) to 77 wt %, Mo is present in an amount within a range of from 46 wt % to 63 wt %, each wt % being based upon combined weight of X, W and Mo.

For supported Keggin-type heteropoly compounds, the support is present in an amount within a range of from greater than 0 wt % to 95 wt %, a combination of metals represented by $M_1$[HPA]$M_2$ is present in a total amount within a range of from 5 wt % to 95 wt %, and $M_3$ is present in an amount within a range of from 0 wt %, preferably greater than 0 wt %, to 10 wt %, each wt % being based upon combined weight of support, the combination of metals represented by $M_1$[HPA]$M_2$, and $M_3$.

Arabic numerals designate Examples (Ex) of the present invention and capital alphabetic letters indicate Comparative Examples (Comp Ex or CEx).

EX 1

(CsCu[PW$_{12}$O$_{40}$]SiO$_2$/Rh/K)

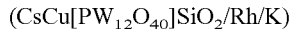

Dropwise add an aqueous solution of copper nitrate hexahydrate (Cu(NO$_3$)$_2$.6H$_2$O) (S. D. Fine, 0.72 grams (g) in 10 milliliters (ml) of water) to 80 ml of a stirred, room temperature (nominally 25 degrees centigrade (° C.) aqueous solution of phosphotungstic acid (8.64 g). Bring the resulting solution to 50° C. and continue stirring for 4 hours (hr). Dropwise add (at an approximate rate of one cubic centimeter per minute (~1 cm$^3$ min$^{-1}$)) thereto an aqueous solution of cesium carbonate (Cs$_2$CO$_3$ (Fluka, 0.48 g) dissolved in 10 ml water) and continue stirring for an hour. Evaporate the resulting solution to dryness at 90° C. to yield a dried solid.

Form a combined solution by mixing an aqueous suspension of 5.01 g of the dried solid in 10 ml of water with 58.82 g of colloidal silica (34 wt % LUDOX colloidal suspension in deionized water, 332.8 millimoles (mmol)) with vigorous stirring at room temperature for an hour. Evaporate the combined solution to dryness at 90° C. to yield dried solids, then calcine the dried solids at 350° C. for 4 hr under static air.

Mix an aqueous solution of rhodium chloride (RhCl$_3$ (Aldrich), 0.21 g dissolved in 10 ml water) with 10 g of the calcined solids, then evaporate the resulting mix to dryness at 100° C. and calcine the dried mix at 300° C. in static air for 5 hr to yield Rh-impregnated solids.

Mix an aqueous solution of potassium carbonate (K$_2$CO$_3$ (Merck, 0.54 g dissolved in 10 ml of water) with 10 g of the Rh-impregnated solids, then evaporate the resulting mix to dryness at 100° C. and calcine the dried mix at 350° C. in static air for 4 hr. The calcined, dried mix has a calculated elemental loading of 0.81 wt % Cs, 0.39 wt % Cu, 2.87 wt % K, 13.49 wt % W, 0.19 wt % P, 0.94 wt % Rh, and 35.14 wt % Si, each wt % being based on total weight of said mix.

Use a high pressure (1500 pounds per square inch gauge (psig) (10.34 megapascals (MPa)) tubular microreactor system to evaluate catalyst activity for converting synthesis gas (syngas) to a mixed alcohol product. Place 1.5 g of the catalyst in the center of a stainless steel reactor (outer diameter (O.D.) of 0.25 inch (0.63 centimeter (cm)) mounted vertically in a furnace. Use thermal mass controllers to transfer syngas (carbon monoxide to hydrogen (CO:H$_2$) ratio of 1:1) from compressed gas cylinders via an activated carbon purifier to the reactor, controlling reactor pressure via an air actuated back pressure regulator located downstream of the reactor. Use an electrically heated aluminum block to control reactor temperature. Before introducing syngas to the reactor, pretreat the catalyst in flowing hydrogen (H$_2$) (150 standard cubic centimeters per minute (s-cm$^3$/min)) at 330° C. for 4 hrs. After pretreatment, lower reactor temperature to 270° C., change the gas flow to 300 s-cm$^3$/min of syngas and then pressurize the reactor to 1500 psig (10.34 MPa).

Analyze products from the reactor by flowing gas phase reactor effluent at ambient pressure (nominally one atmosphere or 0.1 MPa) through a gas sampling valve within a Siemens MAXUM™ gas chromatograph. To avoid condensation of non-volatile products, heat all tubing downstream of the reactor to 160° C. Effect product separation by means of a REOPLEX™ precolumn connected in series with a PORA-PAK™ QS column. Quantify effluent from the PORAPAK column using a calibrated flame ionization detector (FID). Summarize results in Table 1 below.

EX 2

(CsCo[PW$_{12}$O$_{40}$]SiO$_2$/Rh/K)

Replicate Ex 1, but substitute an aqueous solution of cobalt nitrate hexahydrate (Co(NO$_3$)$_2$.6H$_2$O) (S. D. Fine, 0.87 g in 10 ml of water) for the aqueous solution of Cu(NO$_3$)$_2$.6H$_2$O and increase the amount of RhCl$_3$ dissolved in 10 ml of water to 0.42 g. The calcined, dried mix has a calculated elemental loading of 0.79 wt % Cs, 0.36 wt % Co, 2.87 wt % K, 13.51 wt % W, 0.19 wt % P, 0.94 wt % Rh, and 35.14 wt % Si, each wt % being based on total weight of said mix.

EX 3

(CsZn[PW$_{12}$O$_{40}$]SiO$_2$/Rh/K)

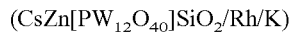

Replicate Ex 1, but substitute an aqueous solution of zinc nitrate hexahydrate (Zn(NO$_3$)$_2$.6H$_2$O) (S. D. Fine, 0.88 g in 10 ml of water) for the aqueous solution of Cu(NO$_3$)$_2$.6H$_2$O, increase the amount of phosphotungstic acid to 8.65 g, and decrease the amount of Cs$_2$CO$_3$ dissolved in 10 ml water to 0.48 g. In addition, change the amount of colloidal silica to 50.69 g and the amount of RhCl$_3$ to 0.22 g. The calcined, dried mix has a calculated elemental loading of 0.81 wt % Cs, 0.40 wt % Zn, 2.87 wt % K, 13.48 wt % W, 0.19 wt % P, 0.94 wt % Rh, and 35.14 wt % Si, each wt % being based on total weight of said mix.

EX 4

(CsNi[PW$_{12}$O$_{40}$]SiO$_2$/Rh/K)

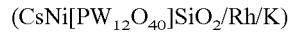

Replicate Ex 1 with several changes. First, substitute an aqueous solution of nickel nitrate hexahydrate (Ni(NO$_3$)$_2$.6H$_2$O (Chemport), 0.86 g in 10 ml of water) for the aqueous solution of Cu(NO$_3$)$_2$.6H$_2$O. Second, change the amount of phosphotungstic acid to 8.64 g. Third, change the amount of Cs$_2$CO$_3$ dissolved in water to 0.48 g. Fourth, change the amount of colloidal silica to 50.65 g. Fifth, change the amount of RhCl$_3$ to 0.22 g. The calcined, dried mix has a calculated elemental loading of 0.81 wt % Cs, 0.36 wt % Ni, 2.87 wt % K, 13.51 wt % W, 0.19 wt % P, 0.94 wt % Rh, and 35.14 wt % Si, each wt % being based on total weight of said mix.

EX 5

(CsCo[PW$_{12}$O$_{40}$]SiO$_2$/Rh/Li)

Replicate Ex 1 with several changes. First, substitute an aqueous solution of cobalt nitrate hexahydrate (Ni(NO$_3$)$_2$.6H$_2$O, 0.87 g in 10 ml of water) for the aqueous solution of Cu(NO$_3$)$_2$.6H$_2$O. Second, change the amounts in the combined solution to 5.00 g of dried solids and 50.07 g of colloidal silica and increase stirring time to two hours. Third, change the amount of RhCl$_3$ to 0.41 g and the amount of calcined solids mixed therewith to 20.00 g. Fourth, substitute aqueous lithium carbonate (Li$_2$CO$_3$ (Sisco), 2.95 g dissolved in 10 ml of water) for the aqueous K$_2$CO$_3$. The calcined, dried mix has a calculated elemental loading of 0.75 wt % Cs, 0.33 wt % Co, 2.39 wt % Li, 12.42 wt % W, 0.17 wt % P, 0.86 wt % Rh, and 32.3 wt % Si, each wt % being based on total weight of said mix.

EX 6

(CsFe[PW$_2$O$_{40}$]SiO$_2$/Rh/K)

Replicate Ex 1 with changes. First, substitute an aqueous solution of ferrous sulphate heptahydrate (Fe(SO$_4$).7H$_2$O, 0.82 g dissolved in 10 ml of water) for the aqueous solution of Cu(NO$_3$)$_2$.6H$_2$O. Second, change the amount of dried solids mixed with colloidal silica to 5.00 g. The calcined, dried mix has a calculated elemental loading of 0.81 wt % Cs, 0.34 wt % Fe, 2.87 wt % K, 13.53 wt % W, 0.19 wt % P, 0.94 wt % Rh, and 35.14 wt % Si, each wt % being based on total weight of said mix.

EX 7

(CsMn[PW$_{12}$O$_{40}$]SiO$_2$/Rh/K)

Replicate Ex 1 with changes. First, substitute an aqueous solution of manganese nitrate tetrahydrate (Mn(NO$_3$)$_2$.4H$_2$O, 0.73 g dissolved in 10 ml of water) for the aqueous solution of Cu(NO$_3$)$_2$.6H$_2$O. Second, substitute aqueous phosphomolybdic acid (8.64 g) for the phosphotungstic acid. Third, change the amount of Cs$_2$CO$_3$ to 0.48 g. Fourth, change the amount of dried solids mixed with colloidal silica to 5.00 g and the amount of colloidal silica to 58.73 g. The calcined, dried mix has a calculated elemental loading of 0.82 wt % Cs, 0.34 wt % Mn, 2.87 wt % K, 13.53 wt % W, 0.19 wt % P, 0.94 wt % Rh, and 35.14 wt % Si, each wt % being based on total weight of said mix.

See Table 2 below for a comparison of Ex 5 and 7 at different reaction temperature, reaction pressure and GHSV combinations.

TABLE 1

| Parameters | Ex and Data | | | | | | |
|---|---|---|---|---|---|---|---|
| | 1 | 2 | 3 | 4 | 5 | 6 | 7 |
| Reaction temperature (° C.) | 340.2 | 340 | 341.5 | 339 | 343 | 343 | 342 |
| Reaction pressure (psig/MPa) | 1495/10.3 | 1498/10.3 | 1498/10.3 | 1502/10.4 | 1504/10.4 | 1502/10.4 | 1502/10.4 |
| GHSV (h$^{-1}$) | 7781 | 8183 | 6428 | 6242 | 8286 | 7863 | 6231 |
| CO conversion (mol %) | 2.74 | 3.44 | 3.05 | 4.99 | 16.4 | 2.3 | 2.0 |
| MeOH selectivity (mol %) | 28.4 | 23.9 | 34.2 | 22.1 | 10.2 | 39.6 | 29.6 |
| EtOH selectivity (mol %) | 14.2 | 14.02 | 14.9 | 15 | 22.5 | 12.6 | 9.01 |
| PrOH selectivity (mol %) | 3.1 | 2.4 | 4.9 | 3.9 | 6.1 | 2.85 | 1.8 |
| Alcohol selectivity (mol %) | 46.2 | 40.08 | 54.5 | 41.9 | 40.6 | 55.9 | 40.6 |
| CH$_4$ selectivity (mol %) | 28.2 | 29.2 | 20.8 | 30.8 | 24.8 | 23.8 | 41.8 |
| C$_2$ HC selectivity (mol %) | 11.5 | 12.7 | 9.1 | 10.4 | 6.7 | 9.4 | 7.7 |
| HC selectivity (mol %) | 49 | 53.8 | 39.7 | 51.7 | 43.3 | 41.5 | 55.9 |
| EtOH Productivity, g/kg$_{cat}$h | 14.1 | 18.8 | 16 | 25.78 | 131.3 | 11.01 | 7.7 |
| PrOH Productivity, g/kg$_{cat}$h | 2.5 | 2.97 | 3.99 | 5.6 | 20.78 | 2.0 | 1.2 |
| Alcohol/HC productivity ratio | 1.72 | 1.38 | 2.53 | 1.43 | 1.49 | 2.54 | 1.36 |

MeOH = methanol; EtOH = ethanol; PrOH = propanol; CH$_4$ = methane; C$_2$ = two carbon atoms; and HC = hydrocarbon

TABLE 2

| Parameters | [5] | [5] | [5] | [5] | [5] | [7] | [7] | [7] |
|---|---|---|---|---|---|---|---|---|
| Reaction temperature (° C.) | 271.0 | 300.8 | 320.7 | 360.1 | 288.2 | 322.6 | 360.7 | 266.4 |
| Reaction pressure (psig/MPa) | 1503.4/ 10.4 | 1499.6/ 10.3 | 1499.6/ 10.3 | 1500.3/ 10.4 | 569.3/ 3.9 | 1502.5/ 10.4 | 1497.2/ 10.3 | 299.8/ 2.1 |
| GHSV ($h^{-1}$) | 8245 | 8259 | 8265 | 8238 | 8258 | 7511 | 7505 | 7499 |
| CO conversion (mol %) | 0.73 | 4.04 | 8.65 | 17.81 | 0.91 | 1.13 | 2.36 | 0.04 |
| MeOH selectivity (mol %) | 43.55 | 24.87 | 14.28 | 5.85 | 12.96 | 37.55 | 28.76 | 87.80 |
| EtOH selectivity (mol %) | 14.21 | 19.11 | 18.16 | 16.53 | 15.78 | 10.21 | 11.69 | 0.00 |
| PrOH selectivity (mol %) | 9.21 | 5.85 | 8.51 | 5.74 | 6.19 | 2.20 | 2.03 | 7.32 |
| Alcohol selectivity (mol %) | 71.36 | 51.27 | 49.19 | 29.95 | 36.10 | 50.27 | 42.99 | 95.12 |
| $CH_4$ selectivity (mol %) | 0.00 | 18.46 | 13.47 | 35.71 | 29.79 | 31.00 | 31.21 | 0.00 |
| $C_2$ HC selectivity (mol %) | 9.47 | 6.52 | 4.85 | 8.93 | 8.38 | 7.80 | 12.45 | 0.00 |
| HC selectivity (mol %) | 28.11 | 36.77 | 29.72 | 59.11 | 57.48 | 45.22 | 53.77 | 4.88 |
| EtOH Productivity, g/$kg_{cat}$-h | 3.99 | 29.54 | 62.84 | 101.22 | 5.90 | 4.71 | 9.90 | — |
| PrOH Productivity, g/$kg_{cat}$-h | 1.77 | 4.77 | 18.11 | 18.54 | 0.83 | 0.79 | 1.37 | 0.07 |
| Alcohol/HC productivity ratio | 4.84 | 2.45 | 2.65 | 0.78 | 1.05 | 2.11 | 1.49 | 41.76 |

MeOH = methanol; EtOH = ethanol; PrOH = propanol; $CH_4$ = methane; $C_2$ = two carbon atoms; and HC = hydrocarbon The data in Tables 1 and 2 demonstrate that when $M_1$ is a mixture of Cs and Cu (Ex 1), Co (Ex 2 and Ex 5), Zn (Ex 3), Ni (Ex 4), Fe (Ex 6) or Mn (Ex 7), $M_2$ is Rh and $M_3$ is either K (Ex 1-4, 6 and 7) or Li (Ex 5), W-based heteropoly compounds function as effective syngas conversion catalysts. From Table 1, Ex 5, with a Li promoter, provides better results in terms of CO conversion and selectivity to ethanol and propanol, relative to methanol, than Ex 1-4, 6 and 7. The data in Table 2 show that at relatively constant pressure and GHSV, an increase in temperature leads to increased CO conversion and selectivity to alcohols whereas a drop in pressure adversely affects CO conversion.

EX 8

($CsCu[PMo_{12}O_{40}]SiO_2/Rh/K$)

Replicate Ex 1 with changes. First, substitute aqueous phosphomolybdic acid (8.64 g) for the phosphotungstic acid. Second, change the amount of $Cs_2CO_3$ to 0.48 g. Third, change the amount of dried solids mixed with colloidal silica to 5 g. Third, change the amount of $RhCl_3$ to 0.21 g, the amount of water in which the $RhCl_3$ is dissolved to 20 ml, and the amount of dried solids mixed with aqueous $RhCl_3$ to 10.00 g. Fourth, for the $RhCl_3$ impregnated material, use a rotavap to remove liquid, reduce the drying temperature to 90° C., change the calcining temperature to 350° C., and change the calcining time to 4 hours. The calcined, dried mix has a calculated elemental loading of 1.24 wt % Cs, 0.59 wt % Cu, 2.87 wt % K, 10.72 wt % Mo, 0.29 wt % P, 0.94 wt % Rh, and 35.14 wt % Si, each wt % being based on total weight of said mix. See Table 3 for results.

EX 9

($CsCo[PMo_{12}O_{40}]SiO_2/Rh/K$)

Replicate Ex 1 with changes. First, substitute aqueous $Co(NO_3)_2.6H_2O$ (S. D. Fine, 0.87 g dissolved in 10 ml of water) for the aqueous solution of $Cu(NO_3)_2.6H_2O$. Second, substitute aqueous phosphomolybdic acid (8.64 g) for the phosphotungstic acid. Third, change the amount of $Cs_2CO_3$ to 0.48 g. Fourth, change the amount of dried solids mixed with colloidal silica to 5.00 g, the amount of colloidal silica to 50.07 g, and mixing time to two hours. Fifth, change the amount of $RhCl_3$ to 0.21 g, the amount of water in which the $RhCl_3$ is dissolved to 30 ml, and the amount of dried solids mixed with aqueous $RhCl_3$ to 20.00 g. Sixth, for the $RhCl_3$ impregnated material, use a rotavap to remove liquid, reduce the drying temperature to 90° C., change the calcining temperature to 350° C., and change the calcining time to 4 hours. The calcined, dried mix has a calculated elemental loading of 1.24 wt % Cs, 0.55 wt % Cu, 2.87 wt % K, 10.74 wt % Mo, 0.29 wt % P, 0.94 wt % Rh, and 35.14 wt % Si, each wt % being based on total weight of said mix. See Table 3 for results.

EX 10

($CsCo[PMo_{12}O_{40}]SiO_2/Rh/Li$)

Replicate Ex 9 with changes. First, change the amount of $RhCl_3$ to 0.41 g. Second, substitute aqueous $Li_2CO_3$ (2.96 g dissolved in 10 ml water) for the aqueous $K_2CO_3$. The calcined, dried mix has a calculated elemental loading of 1.14 wt % Cs, 0.51 wt % Co, 2.39 wt % Li, 9.87 wt % Mo, 0.27 wt % P, 0.86 wt % Rh, and 32.3 wt % Si, each wt % being based on total weight of said mix. See Table 3 for results.

EX 11

($CsFe[PMo_{12}O_{40}]SiO_2/Rh/K$)

Replicate Ex 1 with changes. First, substitute aqueous $FeSO_4.6H_2O$ (S. D. Fine, 0.83 g dissolved in 10 ml of water) for the aqueous solution of $Cu(NO_3)_2.6H_2O$. Second, substitute aqueous phosphomolybdic acid (9.03 g) for the phosphotungstic acid. Third, change the amount of $Cs_2CO_3$ to 0.64 g. Fourth, change the amount of dried solids mixed with colloidal silica to 5 g, suspend the dried solids in 25 ml of water, then add it dropwise with stirring to colloidal silica (58.82 g), and change mixing time to two hours. Fifth, change the amount of $RhCl_3$ to 0.21 g, and the amount of water in which the $RhCl_3$ is dissolved to 30 ml. Sixth, for the $RhCl_3$ impregnated material, use a rotavap to remove liquid, reduce the drying temperature to 90° C., change the calcining temperature to 350° C., and change the calcining time to 4 hours. The calcined, dried mix has a calculated elemental loading of 1.24 wt % Cs, 0.52 wt % Fe, 2.87 wt % K, 10.76 wt % Mo, 0.29 wt % P, 0.94 wt % Rh, and 35.14 wt % Si, each wt % being based on total weight of said mix. See Table 3 for results. See also Table 4 below for a comparison of Ex 9 and Ex 11 at different reaction temperature and GHSV combinations.

EX 12

$(CsCu[PMo_{12}O_{40}]SiO_2/Pd)$

Replicate Ex 1 with changes. First, substitute aqueous $Cu(NO_3)_2$ (0.12 g dissolved in 10 ml of water) for the aqueous solution of $Cu(NO_3)_2 \cdot 6H_2O$. Second, substitute 25 ml of aqueous phosphomolybdic acid (18.06 g or 8 millimoles (mmol)) for the 80 ml of aqueous phosphotungstic acid. Third, change the $Cs_2CO_3$ solution to 0.66 g of $Cs_2CO_3$ dissolved in 5 ml of water. Fourth, dropwise add an aqueous solution of dried solid (0.75 g or 0.24 mmol dissolved in 10 ml of water) to 12.5 g of the colloidal silica to form a mixture, change the drying temperature for the mixture to 100° C., change the calcining temperature for the mixture to 300° C. and the calcining time for the mixture to two hours. Fifth, substitute an aqueous solution of palladium chloride (0.051 g of $PdCl_2$ dissolved in 10 ml of water that contains three drops of hydrochloric acid (HCl) at 55° C. for the aqueous $RhCl_3$ and add it to three g of the calcined colloidal silica mixture. Seventh, use a rotavap to remove liquid from the $PdCl_2$ modified calcined colloidal silica mixture, reduce the drying temperature to 90° C., change the calcining temperature to 350° C., and change the calcining time to 4 hours. The calcined, dried mix has a calculated elemental loading of 10.77 wt % Cs, 1.29 wt % Cu, 46.66 wt % Mo, 1.26 wt % P, 0.29 wt % Pd, and 6.45 wt % Si, each wt % being based on total weight of said mix. See Table 3 for results.

EX 13

$(CsCo[PMo_{12}O_{40}]SiO_2/Pd)$

Replicate Ex 12 with changes. First, substitute aqueous $Co(NO_3)_2$ (0.15 g dissolved in 5 ml of water) for aqueous $Cu(NO_3)_2$. Second, change the amount of phosphomolybdic acid in 25 ml of water to 4.52 g. Third, change the calcining temperature for the colloidal silica mixture to 350° C. and the calcining time to four hours. Fourth, change the aqueous $PdCl_2$ solution to 50.5 milligrams (mg) of $PdCl_2$ dissolved in 9.5 ml of water that contains one ml of HCl. Fifth, dry the $PdCl_2$-modified, calcined colloidal silica mixture at 80° C. using a rotavap, then continue drying at 120° C. for 90 minutes before calcining dried solids at 400° C. in air for two hours. The calcined, dried mix has a calculated elemental loading of 1.20 wt % Co, 10.78 wt % Cs, 46.70 wt % Mo, 1.26 wt % P, 0.29 wt % Pd, and 6.46 wt % Si, each wt % being based on total weight of said mix. See Table 3 for results.

EX 14

$(CsFe[PMo_{12}O_{40}]SiO_2/Pd)$

Replicate Ex 12 with changes. First, substitute aqueous $Fe(NO_3)_3 \cdot 3H_2O$ (0.1374 g dissolved in 10 ml of water) for aqueous $Cu(NO_3)_2$. Second, increase stirring time at 50° C. to four hours. Third, change the $Cs_2CO_3$ solution to 2.61 g of $Cs_2CO_3$ dissolved in 5 ml of water. Fourth, change the drying temperature for the $Cs_2CO_3$ modified combination of $Fe(NO_3)_3 \cdot 3H_2O$ and phosphomolybdic acid to 50° C. The calcined, dried mix has a calculated elemental loading of 10.79 wt % Cs, 1.13 wt % Fe, 46.73 wt % Mo, 1.26 wt % P, 0.29 wt % Pd, and 6.46 wt % Si, each wt % being based on total weight of said mix. See Table 3 for results.

TABLE 3

| Parameters | Ex and Data | | | | | | |
| --- | --- | --- | --- | --- | --- | --- | --- |
| | 8 | 9 | 10 | 11 | 12 | 13 | 14 |
| Reaction temperature (° C.) | 340.2 | 340 | 340.5 | 339 | 341 | 330 | 340.5 |
| Reaction pressure (psig/MPa) | 1495/ 10.3 | 1498/ 10.3 | 1501/ 10.3 | 1502/ 10.4 | 1499/ 10.3 | 1500/ 10.3 | 1503/ 10.4 |
| GHSV ($h^{-1}$) | 7524 | 7560 | 7170 | 7219 | 9927 | 9503 | 9543 |
| CO conversion (mol %) | 17.6 | 27.08 | 29.8 | 28.02 | 9.94 | 19.8 | 10.9 |
| MeOH selectivity (mol %) | 22.3 | 18.7 | 16.2 | 19.8 | 41.8 | 14.9 | 34.1 |
| EtOH selectivity (mol %) | 12.1 | 17.48 | 21.4 | 12.2 | 12.1 | 10.1 | 13.3 |
| PrOH selectivity (mol %) | 5.8 | 8.4 | 6.1 | 6.3 | 4.4 | 4.7 | 5.9 |
| Alcohol selectivity (mol %) | 44.4 | 47.9 | 50.02 | 40.7 | 59.6 | 31.5 | 55.3 |
| $CH_4$ selectivity (mol %) | 31.02 | 24.3 | 28.05 | 29.3 | 24.9 | 66.1 | 25.3 |
| $C_2$ HC selectivity (mol %) | 12.7 | 12.9 | 7.6 | 15.3 | 8.4 | 29.3 | 10.1 |
| HC selectivity (mol %) | 54.8 | 50.4 | 45.6 | 58.1 | 39.4 | 13.7 | 43.6 |
| EtOH Productivity, $g/kg_{cat} \cdot h$ | 80.45 | 156.6 | 235.4 | 106 | 47.5 | 80 | 54.5 |

TABLE 3-continued

| Parameters | 8 | 9 | 10 | 11 | 12 | 13 | 14 |
|---|---|---|---|---|---|---|---|
| PrOH Productivity, g/kg$_{cat}$-h | 25.6 | 48.7 | 62.7 | 43.25 | 12.8 | 27.6 | 18.1 |
| Alcohol/HC productivity ratio | 1.41 | 1.59 | 1.77 | 1.21 | 2.82 | 0.83 | 2.3 |

MeOH = methanol; EtOH = ethanol; PrOH = propanol; $CH_4$ = methane; $C_2$ = two carbon atoms; and HC = hydrocarbon

TABLE 4

| | Catalysts and Data | | | | | |
|---|---|---|---|---|---|---|
| Parameters | [9] | [9] | [9] | [11] | [11] | [11] |
| Reaction temperature (° C.) | 270.33 | 300.61 | 320.16 | 270.33 | 300.18 | 320.61 |
| Reaction pressure (psig/MPa) | 1503.1/10.4 | 1498.4/10.3 | 1500.9/10.3 | 1503.0/10.4 | 1502.1/10.4 | 1506.0/10.4 |
| GHSV (h$^{-1}$) | 7528.1 | 7540.8 | 7534.4 | 7195.2 | 7207.2 | 7207.2 |
| CO conversion (mol %) | 1.78 | 7.20 | 15.88 | 1.86 | 6.53 | 12.59 |
| MeOH selectivity (mol %) | 33.68 | 27.87 | 24.55 | 40.32 | 38.19 | 32.77 |
| EtOH selectivity (mol %) | 16.23 | 20.82 | 20.28 | 16.42 | 18.18 | 18.26 |
| PrOH selectivity (mol %) | 5.53 | 8.14 | 9.13 | 5.07 | 7.18 | 7.40 |
| Alcohol selectivity (mol %) | 57.32 | 59.73 | 57.18 | 63.27 | 65.99 | 61.09 |
| $CH_4$ selectivity (mol %) | 25.53 | 20.03 | 19.70 | 23.96 | 19.25 | 20.57 |
| $C_2$ HC selectivity (mol %) | 6.61 | 8.04 | 9.76 | 5.18 | 6.44 | 8.78 |
| HC selectivity (mol %) | 40.51 | 37.77 | 40.52 | 34.64 | 32.03 | 37.40 |
| EtOH Productivity, g/kg$_{cat}$-h | 10.69 | 53.53 | 114.02 | 11.47 | 46.71 | 83.69 |
| PrOH Productivity, g/kg$_{cat}$-h | 2.80 | 16.32 | 39.88 | 3.04 | 15.27 | 28.65 |
| Alcohol/HC productivity ratio | 2.55 | 2.73 | 2.40 | 3.32 | 3.68 | 2.88 |

MeOH = methanol; EtOH = ethanol; PrOH = propanol; $CH_4$ = methane; $C_2$ = two carbon atoms; and HC = hydrocarbon The data in Tables 3 and 4 demonstrate that the catalysts of Ex 8-14, which have Mo rather than W in the heteropoly compound, also function as effective syngas conversion catalysts.

CEx A ($H_3[PMo_{12}O_{40}]SiO_2$/Rh) (Controlled Experiment)

Dropwise add, with stirring at room temperature, 5 ml of an aqueous solution that contains 2.5 g of phosphomolybdic acid to 29.41 g of colloidal silica (34 wt % LUDOX colloidal suspension in deionized water, 10 g (166.43 millimoles (mmol)) silica). Evaporate the combined solution to dryness at 100° C. to yield dried solids, then calcine the dried solids at 300° C. for two hours in static air.

Mix for one hour, at room temperature and stirring, an aqueous solution of rhodium chloride ($RhCl_3$ (Aldrich), 0.51 g dissolved in 30 ml water) with 20 g of the calcined solids, then evaporate the resulting mix to dryness using a rotovap, then dry further for 4 hours (hr) at 90° C. and calcine the dried mix at 350° C. in static air for 4 hr to yield rhodium impregnated solids. The calcined, dried mix has a calculated elemental loading of 0.15 wt % H, 55.60 wt % Mo, 1.50 wt % P, 0.25 wt % Rh, and 5.43 wt % Si, each wt % being based on total weight of said mix. The balance of the dried, calcined material is oxygen. Evaluate catalyst performance as in Ex 1 and summarize test results in Table 5 below.

TABLE 5

| Parameters | CEx A Data | | | |
|---|---|---|---|---|
| Reaction temperature (° C.) | 270.1 | 300.1 | 320.4 | 340.0 |
| Reaction pressure (psig/MPa) | 1497.6/10.3 | 1498.9/10.3 | 1499.2/10.3 | 1498.3/10.3 |
| GHSV (h$^{-1}$) | 4759.4 | 4763.3 | 4767.2 | 4751.6 |
| CO conversion (mol %) | 9.76 | 12.42 | 25.67 | 47.97 |
| MeOH selectivity (mol %) | 15.10 | 15.89 | 9.67 | 3.00 |
| EtOH selectivity (mol %) | 3.23 | 3.72 | 1.35 | 0.28 |
| PrOH selectivity (mol %) | 0.23 | 0.00 | 0.00 | 0.00 |
| Alcohol selectivity (mol %) | 18.55 | 19.61 | 11.02 | 3.29 |
| $CH_4$ selectivity (mol %) | 40.13 | 45.10 | 51.57 | 57.05 |
| $C_2$ HC selectivity (mol %) | 22.15 | 21.50 | 23.48 | 25.86 |
| HC selectivity (mol %) | 80.64 | 80.39 | 88.98 | 96.71 |
| EtOH Productivity, g/kg$_{cat}$-h | 10.74 | 15.92 | 11.09 | 3.93 |
| PrOH Productivity, g/kg$_{cat}$-h | 0.00 | 0.00 | 0.00 | 0.00 |
| Alcohol/HC productivity ratio | 0.45 | 0.48 | 0.25 | 0.07 |

MeOH = methanol; EtOH = ethanol; PrOH = propanol; $CH_4$ = methane; $C_2$ = two carbon atoms; and HC = hydrocarbon The data in Table 5 demonstrate that catalysts lacking $M_1$ and $M_3$ provide much poorer selectivity to ethanol and propanol than those that contain both $M_1$ and $M_3$ (Tables 1-4).

EX. 15

($Co_1Cs_2[PVMo_{11}O_{40}]/SiO_2$/Rh/Li)

In a 100 ml round bottom flask equipped with a magnetic stir bar, suspend 1.15 g of $H_3PO_4$ (0.01 mol, Acros, 85% wt. solution in water), 0.92 g $V_2O_5$ (S. D. Fine, 0.005 mol) and 15.91 g of $MoO_3$ (0.11 mol, S. D. Fine) in 150 ml of deionized water. Reflux flask contents for 24 hours (hrs) to yield an orange colored solution. Filter the solution to remove residues, then evaporate solvent from the filtered solution at a temperature of 80° C. for 4 hrs, then dry remaining flask contents at 120° C. for 10 hrs to yield a compound referred to as $H_4[PMo_{11}VO_{40}]$ (see. Dimitratos et al., *Catalysis Today.* 122 (2007) 307).

In a 100 ml round bottom flask, stir together for 60 minutes at room temperature (nominally 25° C.) 10 ml of an aqueous solution of the $H_4[PVMo_{11}O_{40}]$ (8 g, 4.49 mmol), and 10 ml of an aqueous solution of cobalt carbonate (0.53 g (4.49 mmol) of $CoCO_3$, S. D. Fine) and cesium carbonate (1.46 g (4.49 mmol) of $Cs_2CO_3$). Dry flask contents at 120° C. for 4 hrs to yield referred as $Co_1Cs_2[PVMo_{11}O_{40}]$.

Dissolve 0.9 g of the dried flask contents in 30 ml of water and add the solution to colloidal silica ($SiO_2$) (Ludox, 40 wt %, 9 g) under stirring at room temperature for 60 minutes to form a mixture. Evaporate the mixture to dryness 100° C. for 4 hrs and calcine the dried mixture at 350° C. for 4 hrs. Add 5 ml of an aqueous solution that contains 0.30 g of rhodium chloride trihydrate ($RhCl_3.3H_2O$) to the calcined dried mixture at room temperature with stirring for 60 min, then repeat drying and calcining. Add 1 ml of an aqueous solution that contains 0.14 g of lithium carbonate ($Li_2CO_3$) (Chemport) with stirring at room temperature for 60 min, then repeat drying and calcining. The dried, calcined material has a calculated elemental loading of: 0.54 wt % Co; 2.43 wt % Cs; 9.64 wt % Mo; 0.28 wt % P; 0.46 wt % V; 0.96 wt % Rh; 0.54 wt % Li; 0.47 wt % C, and 35.94 wt % Si, each wt % being based on total weight of said material. The balance of the dried, calcined material is oxygen. See Table 6 for results.

Use a modification of the microreactor system and process of Ex 1 to effect conversion of syngas and co-fed ethylene to a mixed alcohol product. Substitute a high pressure (508 psig (3.5 MPa)) tubular microreactor system for that of Ex 1 and change the catalyst quantity to 0.35 g. Use thermal mass controllers as in Ex 1 to transfer ethylene along with carbon monoxide, hydrogen and nitrogen (volumetric ratio of ethylene:CO:$H_2$:$N_2$=4.8, 45.1, 45.1, 4.7) from compressed gas cylinders via an activated carbon purifier to the microreactor. Change the pretreatment temperature to 300° C. for 4 hrs.

Analyze products from the reactor as in Ex 1, but change the chromatograph to a Siemens MAXUM™ gas chromatograph by flowing gas phase reactor effluent at ambient pressure (nominally one atmosphere or 0.1 MPa) through a gas sampling valve within Agilent gas chromatograph. To avoid condensation of non-volatile products, heat all tubing downstream of the reactor to 160° C. Effect product separation by means of a an analytical method with three parallel separation trains with (i) a molecular sieve packed column and a HayeSep T packed column, the latter to prevent adsorption of $CO_2$ on molecular sieve column (ii) PoraBOND™ U capillary column, and (iii) a capillary CP Wax separation column. Quantify effluent as in Ex 1 and summarize results in Table 8 below.

EX. 16

($Cs_4[PVMo_{11}O_{40}]/SiO_2/Rh/Li$)

Replicate Ex 15 but substitute 20 ml of an aqueous solution of cesium carbonate (2.93 g (8.98 mmol) of $Cs_2CO_3$, Spectrochem) for the combined cobalt carbonate/cesium carbonate solution to yield a compound referred to as $Cs_4$ [$PVMo_{11}O_{40}$]. The dried, calcined material has a calculated elemental loading of: 4.42 wt % Cs; 8.78 wt % Mo; 0.26 wt % P; 0.42 wt % V; 0.96 wt % Rh; 0.65 wt % Li; 0.47 wt % C, 35.94 wt % Si, each wt % being based on total weight of said material. The balance of the dried, calcined material is oxygen. See Table 6 for results with no ethylene co-feed and Table 8 for results with an ethylene co-feed.

EX. 17

($Co_2[PVMo_{11}O_{40}]/SiO_2/Rh/Li$)

Replicate Ex 15 but substitute 5 ml of an aqueous solution of cobalt carbonate (1.07 g (8.98 mmol) of $CoCO_3$, S. D. Fine) for the combined cobalt carbonate/cesium carbonate solution to yield a compound referred to as $Co_2$ [$PVMo_{11}O_{40}$]. The dried, calcined material has a calculated elemental loading of: 1.19 wt % Co; 10.69 wt % Mo; 0.31 wt % P; 0.52 wt % V; 0.96 wt % Rh; 0.54 wt % Li; 0.47 wt % C, and 35.94 wt % Si, each wt % being based on total weight of said material. The balance of the dried, calcined material is oxygen. See Table 7 for results with no ethylene co-feed and Table 8 for results with an ethylene co-feed.

EX. 18

($Co_1Cu_1[PVMo_{11}O_{40}]/SiO_2/Rh/Li$)

Replicate Ex 15, but substitute 10 ml of an aqueous solution that contains 0.53 g of $CoCO_3$ (4.49 mmol, S. D. Fine) and 0.50 g of $CuCO_3.Cu(OH)_2$ (2.246 mmol) for the combined cobalt carbonate/cesium carbonate solution to yield a material referred to as $Co_1Cu_1[PVMo_{11}O_{40}]$. The dried, calcined material has a calculated elemental loading of: 0.6 wt % Co; 0.64 wt % Cu, 10.67 wt % Mo; 0.31 wt % P; 0.51 wt % V; 0.96 wt % Rh; 0.54 wt % Li; 0.47 wt % C, and 35.94 wt % Si, each wt % being based on total weight of said material. The balance of the dried, calcined material is oxygen. See Table 7 for results with no ethylene co-feed and Table 8 for results with an ethylene co-feed.

TABLE 6

|  | Ex. 15 | Ex. 15 | Ex. 15 | Ex. 15 | Ex. 16 | Ex. 16 | Ex. 16 | Ex. 16 | Ex. 16 |
| --- | --- | --- | --- | --- | --- | --- | --- | --- | --- |
| Temp, ° C. | 300.0 | 320.4 | 340.0 | 360.1 | 270.0 | 300.9 | 320.6 | 340.5 | 360.6 |
| Press, bar | 1500.2 | 1502.4 | 1499.1 | 1499.5 | 1496.7 | 1503.4 | 1502.4 | 1497.4 | 1501.1 |
| GHSV, $h^{-1}$ | 7535.7 | 7548.0 | 7541.8 | 7566.4 | 6507.3 | 6512.7 | 6523.6 | 6507.3 | 6518.2 |
| CO Conv, % | 3.79 | 7.71 | 13.02 | 23.17 | 0.74 | 2.60 | 4.68 | 6.86 | 8.82 |
| S(MeOH), % | 26.60 | 25.52 | 23.98 | 17.90 | 47.43 | 42.05 | 32.35 | 32.10 | 29.92 |
| S(EtOH), % | 19.81 | 19.60 | 18.20 | 15.06 | 19.63 | 19.07 | 17.98 | 17.42 | 16.16 |
| S(PrOH), % | 7.08 | 7.81 | 7.08 | 6.25 | 7.55 | 5.65 | 6.31 | 6.69 | 6.25 |
| S(Alcohols), % | 56.03 | 55.51 | 51.59 | 41.49 | 77.70 | 68.50 | 58.68 | 58.29 | 54.40 |
| S($CH_4$), % | 18.49 | 19.42 | 22.68 | 28.87 | 0.00 | 15.94 | 25.14 | 22.06 | 23.07 |
| S(C2 HC), % | 10.66 | 11.08 | 12.31 | 15.20 | 7.71 | 6.57 | 7.47 | 9.85 | 11.83 |
| S(total HC), % | 42.02 | 42.76 | 47.28 | 57.69 | 18.76 | 29.27 | 40.06 | 40.79 | 44.79 |
| Prod-wt EtOH, g/$kg_{cat}$h | 26.55 | 54.79 | 83.10 | 117.38 | 4.53 | 18.63 | 31.96 | 42.04 | 51.62 |
| Prod-wt-PrOH, g/$kg_{cat}$h | 7.36 | 16.85 | 24.67 | 35.57 | 1.36 | 4.30 | 8.58 | 12.15 | 14.49 |
| Prod OH/HC | 2.34 | 2.25 | 1.89 | 1.22 | 7.99 | 4.29 | 2.60 | 2.54 | 2.16 |

MeOH = methanol; EtOH = ethanol; PrOH = propanol; $CH_4$ = methane; $C_2$ = two carbon atoms; and HC = hydrocarbon; S = selectivity; Conv = conversion; Prod = productivity

TABLE 7

|  | Ex. 17 | Ex. 17 | Ex. 17 | Ex. 17 | Ex. 17 | Ex. 18 | Ex. 18 | Ex. 18 | Ex. 18 |
|---|---|---|---|---|---|---|---|---|---|
| Temp, ° C. | 270.3 | 300.3 | 320.2 | 340.1 | 270.2 | 300.2 | 320.2 | 340.4 | 360.4 |
| Press, bar | 1498.1 | 1498.0 | 1505.9 | 1499.1 | 1502.2 | 1502.8 | 1499.2 | 1501.9 | 1500.3 |
| GHSV, h$^{-1}$ | 7657.0 | 7663.2 | 7663.2 | 7675.7 | 7357.5 | 7382.5 | 7407.5 | 7382.5 | 7413.7 |
| CO Conv, % | 3.63 | 13.11 | 21.21 | 31.72 | 1.75 | 6.08 | 11.35 | 16.78 | 21.48 |
| S(MeOH), % | 26.90 | 26.61 | 22.64 | 19.09 | 38.22 | 32.33 | 29.63 | 27.29 | 24.02 |
| S(EtOH), % | 19.09 | 19.26 | 16.65 | 14.81 | 16.79 | 17.95 | 15.61 | 12.88 | 11.27 |
| S(PrOH), % | 7.25 | 8.08 | 7.54 | 6.67 | 6.40 | 6.54 | 6.44 | 5.12 | 4.67 |
| S(Alcohols), % | 56.65 | 57.26 | 49.97 | 43.31 | 63.95 | 59.31 | 54.10 | 47.27 | 41.72 |
| S(CH$_4$), % | 20.57 | 16.62 | 21.19 | 23.78 | 13.57 | 18.32 | 22.41 | 26.65 | 28.83 |
| S(C2 HC), % | 8.89 | 11.03 | 12.75 | 15.71 | 8.94 | 10.15 | 11.27 | 13.45 | 16.14 |
| S(total HC), % | 42.01 | 41.61 | 48.83 | 55.75 | 35.13 | 40.18 | 45.43 | 52.19 | 58.22 |
| Prod-wt EtOH, g/kg$_{cat}$-h | 24.41 | 84.70 | 120.24 | 149.62 | 11.15 | 39.19 | 62.57 | 73.24 | 80.98 |
| Prod-wt-PrOH, g/kg$_{cat}$-h | 7.23 | 27.74 | 41.83 | 50.10 | 3.60 | 12.13 | 21.70 | 23.79 | 26.44 |
| Prod OH/HC | 2.35 | 2.40 | 1.76 | 1.33 | 3.36 | 2.64 | 2.12 | 1.63 | 1.29 |

MeOH = methanol; EtOH = ethanol; PrOH = propanol; CH$_4$ = methane; C$_2$ = two carbon atoms; and HC = hydrocarbon; S = selectivity; Conv = conversion; Prod = productivity The data in Tables 6 and 7 demonstrate that one can to substitute a transition metal like vanadium for at least a portion of Mo. Similar results should follow with replacement of at least a portion of W as well as substitution with other transition metals, specifically Cu, Co, Fe, Ti, Pd, Ru, and Mn based upon teachings contained in Journal of Molecular Catalysis volume 114, pages 129-130 (1996). A complete replacement of the counter cation of the Keggin-type heteropoly compounds with CO activating elements like Co, Cu rather than partial replacement of the cations with these elements and alkali brings advantage towards higher CO conversion.

TABLE 8

|  | Ex. 15 | Ex. 15 | Ex. 16 | Ex. 16 | Ex. 18 | Ex. 18 | Ex. 18 | Ex. 18 | Ex. 18 |
|---|---|---|---|---|---|---|---|---|---|
| PRESSURE | 35 | 35 | 35 | 35 | 35 | 35 | 35 | 35 | 35 |
| Temperature, ° C. | 300.4 | 321.1 | 300.5 | 320.3 | 281.7 | 301.2 | 320 | 320 | 320 |
| Ethylene Conv, % | 16.50 | 35.48 | 20.00 | 30.63 | 27.04 | 60.13 | 83.57 | 83.57 | 83.57 |
| S(CO$_2$), % | 8.77 | 9.43 | 5.54 | 6.72 | 3.88 | 4.25 | 6.76 | 6.76 | 6.76 |
| S(Ethane), % | 50.65 | 59.45 | 54.18 | 63.74 | 61.24 | 68.20 | 69.05 | 69.05 | 69.05 |
| S(Propanal), % | 2.80 | 1.54 | 2.68 | 1.49 | 1.55 | 1.00 | 0.76 | 0.76 | 0.76 |
| S(Methanol), % | 2.02 | 1.71 | 1.74 | 1.45 | 1.51 | 1.44 | 1.52 | 1.52 | 1.52 |
| S(Ethanol), % | 2.18 | 1.71 | 1.22 | 1.06 | 1.17 | 1.04 | 1.11 | 1.11 | 1.11 |
| S(Propanol), % | 20.39 | 13.94 | 27.89 | 14.01 | 24.64 | 18.08 | 10.56 | 10.56 | 10.56 |
| S(propanal + propanol), % | 23.20 | 15.47 | 30.56 | 15.49 | 26.19 | 19.08 | 11.32 | 11.32 | 11.32 |

S = selectivity; Conv = conversion, reduction condition: 300° C. for 4 hr under H$_2$ flow 100 ml/min at atmospheric pressure.

The data in Table 8 demonstrates that catalysts having a structure represented by general formula M$_1$[HPA]M$_2$M$_3$ effectively convert co-fed syngas and ethylene to mixed alcohol products.

What is claimed is:

1. A process for converting synthesis gas to an oxygenate, which process comprises contacting a mixture of hydrogen and carbon monoxide with a catalyst based on a transition metal-containing, Keggin-type heteropoly compound under conditions of temperature, pressure and gas hourly space velocity sufficient to convert said mixture to at least one alcohol wherein the alcohol is a one carbon to six carbon alcohol, the catalyst having a structure represented by general formula M$_1$[HPA]M$_2$M$_3$ where M$_1$ is at least one metal selected from a group consisting of alkali metals, alkaline earth metals, zinc, cobalt, iron, manganese, nickel or copper where sum net charge of M$_1$ is equal to net negative charge of HPA anion; HPA is represented by general formula [XMo$_{12-(x+y)}$W$_x$T$_y$O$_{40}$] wherein Mo is molybdenum, W is tungsten, T is at least one transition metal selected from vanadium, copper, cobalt, iron, titanium, palladium, ruthenium, and manganese, x=0-12, y=0-3 provided that x+y=0-12, and X is at least one of phosphorous, silicon, germanium, and cobalt; M$_2$ is at least one of rhodium, palladium, iridium, rhenium, ruthenium, platinum and gold, and M$_3$ is an optional material that is at least one alkali or alkaline earth metal, provided that when M$_1$ is an alkali metal or an alkaline earth metal, it is a different alkali metal or alkaline earth metal than M$_3$, when M$_1$ is cobalt, X is at least one of phosphorous, silicon and germanium.

2. The process of claim 1, wherein the conditions of temperature, pressure and gas hourly space velocity include at least one of a temperature is within a range of from 200° C. to 450° C., a pressure is within a range of from 200 psig (1.38 MPa) to 5,000 psig (34.47 MPa), and a gas hourly space velocity is within a range of 300 hr$^{-1}$ to 25,000 hr$^{-1}$.

3. The process of claim 1, wherein the catalyst further comprises at least support selected from silicas, aluminas, magnesias, zirconias, titanias, tungsten oxides, zinc oxide or mixtures thereof, and modified supports selected from zirconia-modified silica, tungstated silica, zeolites, double layered hydroxides, and clays.

4. The process of claim 1, wherein the mixture of hydrogen and carbon monoxide has a ratio of hydrogen to carbon monoxide within a range of from 10:1 to 1:10.

5. The process of claim 1, wherein M$_3$ is potassium, lithium or a mixture of potassium and lithium.

6. The process of claim 1, wherein X is phosphorous and x=0.

7. The process of claim 1, wherein $M_2$ is rhodium.

8. The process of claim 1, wherein $M_1$ is a combination of cesium and cobalt.

9. The process of claim 1, wherein the mixture of carbon monoxide and hydrogen further comprises an amount of an olefin selected from a group consisting of ethylene, propylene and butylene.

\* \* \* \* \*